United States Patent
Koike et al.

(10) Patent No.: US 6,844,021 B2
(45) Date of Patent: Jan. 18, 2005

(54) OIL OR FAT COMPOSITION

(75) Inventors: Shin Koike, Tokyo (JP); Takatoshi Murase, Tochigi (JP); Tadashi Hase, Tochigi (JP)

(73) Assignee: Kao Corporation, Tokyo (JP)

( * ) Notice: Subject to any disclaimer, the term of this patent is extended or adjusted under 35 U.S.C. 154(b) by 153 days.

(21) Appl. No.: 10/132,504

(22) Filed: Apr. 26, 2002

(65) Prior Publication Data

US 2003/0054082 A1 Mar. 20, 2003

(30) Foreign Application Priority Data

Apr. 26, 2001 (JP) ........................................ 2001-129437

(51) Int. Cl.$^7$ ........................ A23D 9/007; A61K 31/202
(52) U.S. Cl. .................... 426/611; 426/330.6; 426/601; 514/558; 514/560; 514/909
(58) Field of Search .................................. 426/601, 611

(56) References Cited

U.S. PATENT DOCUMENTS

| | | | | |
|---|---|---|---|---|
| 4,656,045 | A | * 4/1987 | Bodor et al. ................. | 426/601 |
| 6,448,292 | B2 | * 9/2002 | Koike et al. ................. | 514/558 |
| 6,495,536 | B1 | * 12/2002 | Masui et al. ................. | 514/182 |
| 2002/0142089 | A1 | * 10/2002 | Koike et al. ................. | 426/607 |
| 2003/0054082 | A1 | * 3/2003 | Koike et al. ................. | 426/601 |
| 2003/0072858 | A1 | * 4/2003 | Koike et al. ................. | 426/417 |
| 2003/0198727 | A1 | * 10/2003 | Koike et al. ................. | 426/601 |

OTHER PUBLICATIONS

Anon. 1982. The American Heritage Dictionary, 2$^{nd}$ college edition. 1982. p. 459 & 1351.*
U.S. Appl. No. 10/132,504, filed Apr. 26, 2002, Koike et al.
U.S. Appl. No. 10/761,358 filed Jan. 22, 2004, Koike et al.
U.S. Appl. No. 10/343,831, filed Feb. 10, 2003, Koike et al.
U.S. Appl. No. 10/343,748, filed Feb. 6, 2003, Koike et al.
U.S. Appl. No. 10/343,742, filed Feb. 6, 2003, Koike et al.
U.S. Appl. No. 10/019,427, filed Dec. 31, 2001, Masui et al.
U.S. Appl. No. 10/009,494, filed Apr. 8, 2002, Masui et al.
U.S. Appl. No. 10/132,504, filed Apr. 26, 2002, Koike et al.
U.S. Appl. No. 10/101,606, filed Mar. 21, 2002, Kataoka et al.
U.S. Appl. No. 10/132,504, filed Apr. 26, 2002, Koike et al.
U.S. Appl. No. 10/032,493, filed Jan. 2, 2002, Koike et al.
U.S. Appl. No. 10/132,504, filed Apr. 26, 2002, Koike et al.

* cited by examiner

*Primary Examiner*—Carolyn Paden
(74) *Attorney, Agent, or Firm*—Oblon, Spivak, McClelland, Maier & Neustadt P.C.

(57) ABSTRACT

The oil or fat composition of the invention contains a monoacylglycerol and/or a diacylglycerol in a total amount of 5–100 wt. % and which exhibits an index of stability against oxidation (induction time as measured through a Rancimat test conducted at 100° C.) of 7 or higher, wherein the monoacylglycerol and/or the diacylglycerol contain, as fatty acid constituents, ω3 unsaturated fatty acids in amounts of 15–90 wt. %. Through ingestion thereof in a small amount without drastically changing the person's lifestyle, the highly harmless oil/fat composition of the present invention provides effects for reducing and preventing accumulation of body fat, for reducing and preventing accumulation of visceral fat, and for prevention and treatment of obesity; and exerts an excellent prevention and treatment effect on lifestyle related diseases through long-term ingestion. Thus, the composition of the present invention is useful for foods, pharmaceuticals and pet food or feed.

21 Claims, No Drawings

OIL OR FAT COMPOSITION

BACKGROUND OF THE INVENTION

1. Field of the Invention

The present invention relates to an oil or fat composition which is effective for reduction of body fat and visceral fat for the prevention of accumulation of such fats, and for prevention and treatment of obesity and related conditions; which exerts an excellent prevention and treatment effect on life-style related diseases caused by accumulated fats, through long-term ingestion of the composition; and which is useful for foods, pharmaceuticals, and pet food or feed.

2. Discussion of the Background

Obesity and life-style related diseases such as hyperlipemia are said to be prevented and treated by changing aspects of the person's lifestyle, such as unbalanced diet and lack of physical exercise. Particularly, they are prevented through reduction of body fat, inter alia, visceral fat, so as to suppress obesity.

Among nutrients, oil and fat, having a high calorific value (9 kcal/g), promote obesity, and induce life-style related diseases. Thus, a wide range of studies have been conducted on anti-obesity oils and fats. For example, U.S. Pat. No. 3,600,186 discloses a technique employing a polyester which is derived from a sucrose fatty acid and is not absorbed by the body. However, the polyester raises problems such as anal leakage and inhibition of absorption of fat-soluble vitamins.

Apart from the polyester, conjugated linoleic acid, fish oil, and perilla oil have been proven to exert effect on reduction of body fat in animal experiments (see *Lipids* 32, 853 (1997); *J. Agric. Food Chem.* 46, 1225 (1998); *Metabolism* 39, 217 (1990); etc.). However, these materials fail to exert ensured effect when administered in small amounts.

Other approaches are based on a glyceride structure that is harmless and causes no adverse side effects during long-term administration. Examples of such approaches include employment of a cholesterol-reducing agent (Japanese Patent Application Laid-Open No. 63-104917); a serum-triglyceride-concentration-reducing agent (Japanese Patent Application Laid-Open Nos. 4-300825 and 5-310567); a body-weight-gain-suppressing agent (Japanese Patent Application Laid-Open No. 4-300826); an agent for preventing and treating fatty liver (Japanese Patent Application Laid-Open No. 4-300828); and a liquid oil composition for general use (U.S. Pat. No. 6,004,611). These approaches are based on an effect attributed to monoglyceride or diglyceride structure and are considered highly safe approaches, in that adverse effects such as anal leakage and inhibition of absorption of fat-soluble vitamins are avoided.

In order to fully attain such effects in treating obesity, a monoglyceride and/or a diglyceride, instead of a triglyceride, must be ingested in large amounts in the form of a product such as cooking oil. However, the cooking oil for attaining these effects is not suitable for a large amount of daily ingestion. In contrast, WO 01/10989 discloses that a diglyceride prepared from an ω3 unsaturated fatty acid having 20 or more carbon atoms exerts the above effects through ingestion thereof in a small amount, and Japanese Patent Application Laid-Open No. 2001-64672 discloses an oil or fat composition containing a monoglyceride and/or diglyceride as an effective ingredient. However, the monoglyceride and/or diglyceride remain unsatisfactory, and demand exists for an oil or fat composition which contains a monoglyceride and/or diglyceride exerting efficacy through ingestion in a smaller amount and which can be easily ingested over a long period of time.

SUMMARY OF THE INVENTION

The present inventors have carried out extensive studies in order to overcome the aforementioned points, and have found that an oil or fat composition which contains a monoglyceride and/or diglyceride containing specific fatty acids as fatty acid constituents, and which exhibits a specific degree of stability against oxidation is, surprisingly, remarkably effective for reduction of body fat and visceral fat, prevention of accumulation of such fats, and prevention and treatment of obesity; that the composition exerts an excellent prevention and treatment effect against conditions; i.e., life-style related diseases caused by accumulated fats; and that the composition is useful for foods, pharmaceuticals, and pet food or feed.

Thus, an object of the present invention is to provide an oil or fat composition which is effective, through ingestion thereof in a small amount without requiring drastic changes in the person's lifestyle, for reduction of body fat and visceral fat, for prevention of the accumulation of such fats, and prevention and treatment of obesity; which exerts an excellent prevention and treatment effect against conditions; i.e., life-style related diseases caused by accumulated fats; and which is useful for foods, pharmaceuticals, and pet food or feed.

Accordingly, in a first aspect of the present invention, there is provided an oil or fat composition which comprises a monoglyceride and/or a diglyceride in a total amount of 5–100 wt. % and which exhibits an index of stability against oxidation (induction time as measured through a Rancimat test at 100° C.) of 7 or higher, wherein the monoglyceride and/or the diglyceride contains, as fatty acid constituents thereof, ω3 unsaturated fatty acids in amounts of 15–90 wt. %.

In another aspect of the invention, there is provided a food comprising the aforementioned oil or fat composition.

In still another aspect of the invention, there is provided an agent for reducing or preventing accumulation of body fat, for reducing or preventing accumulation of visceral fat, or for preventing or treating obesity, which agent comprises the oil or fat composition.

In yet another aspect of the invention, there is provided a method for reducing or preventing accumulation of body fat, which comprises ingesting the aforementioned oil or fat composition.

In still another aspect of the invention, there is provided a method for reducing or preventing accumulation of visceral fat, which comprises ingesting the aforementioned oil or fat composition.

In yet another aspect of the invention, there is provided a method for preventing or treating obesity, which comprises ingesting the aforementioned oil or fat composition.

In still another aspect of the invention, there is provided a pet food or feed containing the aforementioned oil or fat composition.

DETAILED DESCRIPTION OF PREFERRED EMBODIMENTS

The oil or fat composition of the present invention (hereinafter may be referred to as the oil/fat composition of the present invention) contains a monoglyceride and/or a diglyceride in a total amount of 5–100 wt. % (hereafter wt.

% will be referred to simply as %), preferably 15–100%, more preferably 40–100%, particularly preferably 60–99%, most preferably 80–95%. Typically, the diglyceride is a mixture containing a 1,3-diglyceride and a 1,2-diglyceride in a proportion by weight of approximately 7:3. Of these, 1,3-diglyceride is preferred. Typically, the monoglyceride is a mixture containing a 1-monoglyceride and a 2-monoglyceride in a proportion by weight of approximately 9:1. Of these, 1-monoglyceride is preferred.

The monoglyceride and the diglyceride may be used singly or in combination, preferably in combination.

The monoglyceride and diglyceride used in the present invention contain, as fatty acid constituents, ω3 unsaturated fatty acids in amounts of 15–90%, in view of their effects and stability against oxidation. The percentage of the ω3 unsaturated fatty acids is preferably 20–80%, more preferably 30–70%, particularly preferably 40–65%. The term "ω3 unsaturated fatty acid" herein means a fatty acid having a first unsaturated bond at the third carbon atom from the ω position and having at least two carbon-carbon unsaturated bonds. Examples of such fatty acids include α-linolenic acid (C18:3, all cis); stearidonic acid (C18:4, all cis); eicosapentaenoic acid (EPA, C20:5, all cis); docosapentaenoic acid (DPA, C22:5, all cis); and docosahexaenoic acid (DHA, C22:6, all cis). Of these, α-linolenic acid, EPA, and DHA are preferred, with α-linolenic acid being more preferred.

The monoglyceride and diglyceride used in the present invention preferably contain, as fatty acid constituents, C16–C22 unsaturated fatty acids in amounts of 55–100% in view of their effects, flavors, and tastes. The percentage of the unsaturated fatty acids is more preferably 70–100%, particularly preferably 80–100%, most preferably 90–97%.

The monoglyceride and diglyceride used in the present invention preferably have, as fatty acid constituents, a ratio (by weight) of cis-ω3 unsaturated fatty acids to (cis-ω6 unsaturated fatty acids+saturated fatty acids+trans-unsaturated fatty acids) of preferably 1–6, more preferably 1.2–5, particularly preferably 1.4–4, most preferably 1.5–3, in view of effects, stability, and fatty acid balance. As used herein, the term "trans-unsaturated fatty acid" refers to an unsaturated fatty acid in which one or more double bonds are of trans configuration and which is identified through the IR absorption spectrometry method (Japan Oil Chemists' Society: Standard Methods for the Analysis of Fats, Oil, and Related Materials 2.4.4.2-1996), gas chromatography method (*J. Amer. Oil Chem. Soc.*, 70, 425 (1993)), etc. The trans-unsaturated fatty acid content is particularly preferably 5% or less.

The monoglyceride and diglyceride used in the present invention preferably contain, as fatty acid constituents, C8–C12 medium-chain fatty acids in amounts of 5% or less, in view of flavor and taste. The percentage of the medium-chain fatty acids is more preferably 2% or less, particularly preferably 0.5% or less, most preferably 0%.

The oil/fat composition of the present invention contains a triglyceride in an amount of 0–95%. In view of flavor and stability against oxidation, the amount is preferably 1–85%, more preferably 5–80%, further preferably 5–60%, particularly preferably 5–40%. The triglyceride preferably contains, as fatty acid constituents, 55–100% of which are preferably C16–C22 unsaturated fatty acids, in view of effects, flavors, and tastes. The percentage is more preferably 70–100%, further preferably 80–100%, particularly preferably 90–97%. In view of stability against oxidation, the triglyceride has preferably, as fatty acid constituents, 0–40% of ω3 unsaturated fatty acids. The percentage is more preferably 0–30%, further preferably 0–20%, particularly preferably 0–15%.

Free fatty acids contained in the oil/fat composition of the present invention provide unfavorable tastes and therefore the amount thereof should be controlled to 10% or less, preferably 5% or less, more preferably 2.5% or less, particularly preferably 1% or less, most preferably 0.5% or less from the standpoint of flavor.

The oil/fat composition of the present invention containing a monoglyceride and/or a diglyceride can be produced through methods known to those of ordinary skill in the art without undue experimentation. For example, there can be employed a method disclosed in Japanese Patent Application Laid-Open No. 4-300825 including transesterification of glycerin and triglyceride oil such as perilla oil, linseed oil, or fish oil. Alternatively, esterification of a glyceride and a fatty acid derived from an oil/fat may also be employed. These reactions can be performed through a chemical method employing a metallic catalyst, or through a biochemical method employing an oil/fat-hydrolase such as lipase. Of these, the biochemical method is preferably employed, in view of prevention of deterioration such as coloring or isomerization.

The index of stability against oxidation of the present invention corresponds to an induction time (hr) measured through a Rancimat test of an oil/fat at 100° C., and is obtained through the following method (Japan Oil Chemists' Society: Standard Methods for the Analysis of Fats, Oil, and Related Materials 2.5.1.2-1996, modified CDM test). Specifically, the test temperature (120° C.) is changed to 100° C. Clean air is fed to an oil/fat sample, while the sample is heated in a vessel, to thereby yield a volatile substance through oxidation. The substance is collected in water, and the period of time (hr) to the point at which the conductivity of the mixture is sharply elevated is measured. In the present invention, the index of stability against oxidation is required to be 7 or more, preferably 9–50, more preferably 11–40, particularly preferably 15–30, most preferably 20–30. When the index of stability against oxidation is 7 or more, the oil/fat composition of the present invention containing the aforementioned monoglyceride and/or diglyceride which contain ω3 unsaturated fatty acids as fatty acid constituents develops remarkable effects of reducing body fat and visceral fat; preventing accumulation of such fats; and preventing and treating obesity. If the composition is ingested over a long period of time, an excellent prevention and treatment effect against conditions; i.e., life-style related diseases caused by accumulated fats, is remarkably developed. In view of flavors, appearance, and manageability, the index of stability against oxidation is preferably 50 or less.

Adjusting the index of stability against oxidation of the oil/fat composition of the present invention to 7 or more can be accomplished by any method. For example, addition of an anti-oxidant; dilution by use of an oil/fat containing a small amount of fatty acid moieties derived from unsaturated fatty acids having 4 or more carbon-carbon double bonds; or transesterification may be employed. In view of efficacy, addition of an anti-oxidant is preferred. Examples of the anti-oxidant include those added in foods or pharmaceuticals; e.g., vitamin A, vitamin C, vitamin E, phospholipids, polyphenols, butylhydroxytoluene (BHT), butylhydroxyanisole (BHA), tert-butylhydroquinone (TBHQ), propyl gallate, and rosemary extracts. These anti-oxidants may be used in combination of two or more species.

Examples of vitamin A include retinol, retinal, dehydroretinoic acid, and carotene. Examples of vitamin C include ascorbic acid, ascorbic acid palmitic acid esters, and ascorbic acid stearic acid esters. Examples of vitamin E include a-tocopherol, β-tocopherol, γ-tocopherol, and δ-tocopherol, with γ-tocopherol and δ-tocopherol being preferred. Examples of phospholipids include phosphatidyl choline, phosphatidyl ethanolamine, phosphatidyl serine, phosphatidyl inositol, phosphatidic acid, and lyso derivatives thereof. The anti-oxidant content in the oil/fat composition is preferably 0.02–5%, more preferably 0.03–3%, particularly preferably 0.05–2%, in view of effects and coloring.

Examples of the polyphenols include natural anti-oxidant components such as catechin and flavonoids, with catechin being preferred. The polyphenol content of the oil/fat composition, as reduced to net weight, is preferably 0.02–2%, more preferably 0.03–1.5%, particularly preferably 0.05–1%, in view of effects and coloring.

The rosemary extract is obtained by drying leaves of rosemary, which belongs to the Perilla family, pulverizing the dried leaves, and subjecting the resultant pulverized material to extraction with water, hot water, hexane, ethanol, acetone, ethyl acetate, or a mixture of any of these solvents. In the present invention, not only can the thus-produced extract be used, but so can oleoresin products formulated by use of the extract, as can formulations containing rosemanol, carsonol, or isorosemanol, which are constituents of the extract. From the viewpoint of excellent flavor, these extracts are preferably subjected to deodorizing treatment through reduction in pressure, heating under reduced pressure, supercritical fluid extraction, or column adsorption. Hereinafter, the thus-obtained deodorized extracts will be referred to simply as deodorized extracts. The amount of residual solvent in the deodorized extracts is preferably 20 ppm or less, more preferably 15 ppm or less. Examples of commercial products of rosemary extract include HERBER ROCKS TYPE O ,HERBER ROCKS TYPE HT-O, HERBER ROCKS TYPE 25, DUOLITE NMH, and DUOLITE NM-1 (all these are products of Calsec), and LEOMEAL E and LEOMEAL IO (these two are products of Lion Co., Ltd.). In order to impart excellent anti-oxidation property to the oil/fat composition of the present invention, the amount of any of these rosemary extracts to be incorporated into the composition is preferably 0.02 to 0.5%, more preferably 0.05 to 0.35%, even more preferably 0.1 to 0.3%, as reduced to the net weight of the extract; i.e., excluding water and organic solvents.

When the oil/fat composition of the present invention contains an organic carboxylic acid such as a hydroxycarboxylic acid or a dicarboxylic acid or a salt thereof, hydrolysis of the composition is desirably prevented. Examples of the carboxylic acid include citric acid, malic acid, and tartaric acid, with citric acid being preferred. Examples of the salt of the organic carboxylic acid include alkali metal salts and alkaline earth metal salts. Of these, sodium salts and calcium salts are preferred. The amount of the carboxylic acid or salt thereof based on the oil/fat composition is preferably 0.001% or more, more preferably 0.001–0.2%, particularly preferably 0.0015–0.15%, most preferably 0.002–0.1%.

In addition, a crystallization inhibitor is preferably added to the oil/fat composition of the present invention, in view of appearance and manageability. The HLB value of the crystallization inhibitor is preferably 4 or below, more preferably 3 or below, while the HLB value of each compound was determined by an empirical method fit for the compound such as Griffin's formula (*J. Soc. Cosmet. Chem.*, 1, 311 (1949)). Examples of the crystallization inhibitor used in the present invention include polyol fatty acid esters such as polyglycerin condensed ricinoleic acid esters, polyglycerin fatty acid esters, sucrose fatty acid esters, sorbitan fatty acid esters, polyoxyethylene sorbitan fatty acid esters, and propylene glycol fatty acid esters. The oil/fat composition of the present invention preferably contains a crystallization inhibitor in an amount 0.02–0.5%, particularly preferably 0.05–0.2%.

When the oil/fat composition of the present invention is administered to the human body in a form of foods or pharmaceuticals, the daily dose for adults typically falls within a range of 0.1–25 g, preferably within a range of 0.1–10 g, more preferably within a range of 0.2–5 g, especially within a range of 0.2–2.5 g. Preferably, the composition is administered once or in several portions per day.

Through incorporation of the oil/fat composition of the present invention into foods, long-term ingestion of the foods is realized, advantageously leading to attainment of the effects of preventing and treating life-style related diseases. The food of the present invention may include, in addition to general food products, foods for promoting health through specific functions, such as health foods, functional foods, and foods for specified health use. In order to prepare these specific foods, the food of the present invention may be formed into tablets, granules, powders, etc., rather than as food products. Examples of the food products include bakery-related products such as breads, cakes, cookies, pies, pizza crusts, and bakery mixtures; O/W type oil/fat processed products such as dressings, mayonnaise sauces, coffee creamers, and whipped creams; W/O type oil/fat processed products such as margarines, spreads, and butter creams; snack foods such as chocolates, potato chips, ice creams, and desserts; milk products such as milk, cheese, and yogurt; beverages; sauces; liquid seasonings for grilled meat; peanut butter; shortenings for frying and baking; processed meats such as hams, sausages, and hamburgers; noodles; frozen foods; retort-pouched foods; and cooking oils for deep-frying such as tempura, fries and the like, as well as frizzling. These food products are prepared from the oil/fat composition of the present invention and typical food raw materials in accordance with the target food product. Since the oil/fat composition of the invention can be incorporated into a variety of foods, the composition can be ingested daily without any special effort. Generally, the oil/fat composition of the present invention is incorporated into a food in an amount, which varies in accordance with the type of the food, of preferably 0.05–100%, particularly preferably 0.5–80%.

In connection with preparation of pharmaceuticals, when any of the food products contains an oil/fat originating from food raw materials, the ratio of the oil/fat originating from food raw materials to the oil/fat composition of present invention is preferably 95:5 to 1:99, more preferably 95:5 to 5:95, further preferably 85:15 to 5:95, particularly preferably 60:40 to 5:95.

The pharmaceuticals containing the oil/fat composition of the present invention include those for peroral administration. Examples of the form include solid forms such as powders, granules, capsules, pills, and tablets; and liquid forms such as solutions, suspensions, and emulsions. The pharmaceuticals for peroral administration may be prepared from the oil/fat composition of the present invention, and any of additives such as vehicles, disintegrants, binders, lubricants, surfactants, alcohol, water, water-soluble polymers, sweetening agents, flavors, and sour agents, which are generally used in accordance with the type of the pharmaceuticals. Examples of types of the pharmaceuticals which are administered to patients orally include those for reducing body fat or preventing accumulation of body fat; those for reducing visceral fat or preventing accumulation of visceral fat; those for prevention and treatment of obesity; and those for prevention and treatment of life-style related diseases. Generally, the amount of the oil/fat composition of the present invention contained in a pharmaceutical for peroral administration, which varies in accordance with use and form of the pharmaceutical, is preferably 0.05–100%, particularly preferably 1–50%.

The monoglyceride and/or diglyceride content of the oil/fat composition is preferably 15–100%, more preferably 40–100%, especially 60–99%, most preferably 80–95%. The ω3 fatty acid content in the fatty acid constituents of the monoglyceride and/or diglyceride is preferably 20–80%, more preferably 30–70%, especially 40–65%. The index of stability against oxidation is preferably required to be 7–50, more preferably 11–40, especially 15–30, most preferably 20–30.

In the case in which an anti-oxidant is added to the oil/fat composition of the present invention for producing a food or a pharmaceutical, the anti-oxidant and a monoglyceride and/or a diglyceride are not required to be mixed in advance, so long as a predetermined amount of each component is incorporated into the food or the pharmaceutical.

The oil/fat composition of the present invention can be used for a pet food or feed. In the present invention, the term "pet food" means pet food for dogs, cats, and the like pets, whereas the term "feed" means feed for animals such as pigs, poultry, and fish.

The pet food or feed of the present invention contains 1–40% of the oil/fat composition, preferably 1–30%, more preferably 2–20%. The oil/fat composition may be substituted for the part or whole of the existing oil or fat content in the pet food or feed.

The base of the pet food or feed of the present invention is prepared by mixing the oil/fat composition and the other components to be added as needed with meats, proteins, grains, brans, starch cakes, saccharides, vegetables, vitamins, and minerals.

Examples of the meats include livestock meats such as beef, pork, chicken, mutton, lamb, and fish meat. Examples of the proteins include animal proteins such as casein, and vegetable proteins such as soybean protein. Examples of the grains include wheat, barley, rye, milo, and corn, those of brans include rice bran and wheat bran, and those of the starch cakes include soybean cake. The total content of the meats, proteins, grains, brans, and starch cakes is preferably 5–95% of the pet food or feed.

Examples of the saccharides include oligosaccharides, sugar, sucrose, and molasses and their content is preferably 5–80% of the pet food or feed.

As the vegetables, vegetable extracts are usable and the vegetable content is preferably 1–30% of the pet food or feed.

Examples of the vitamins include A, $B_1$, $B_2$, D, E, niacin, pantothenic acid, and carotene and their content is preferably 0.05–10% of the pet food or feed.

Examples of the minerals include calcium, phosphorus, sodium, potassium, and iron and their content is preferably 0.05–10% of the pet food or feed.

In addition, the pet food or feed of the present invention may contain ordinarily employed additives such as gelling agent, shape retainer, pH regulator, seasoning, antiseptic, and nutrition supplement.

From the viewpoint of the effect of reducing cholesterol, the food or pharmaceutical of the present invention contains a phytosterol in an amount of 0.05% or more, particularly 0.3% or more. No particular limitation is imposed on the upper limit of the amount of the phytosterol, and the amount preferably falls within a range of 0.05–20%. Examples of the phytosterol include α-sitosterol, β-sitosterol, stigmastanol, campesterol, α-sitostanol, β-sitostanol, stigmastanol, campestanol, and cycloartenol, as well as esters thereof, such as fatty acid esters, ferulic acid esters, and cinnamic acid esters.

Having generally described this invention, a further understanding can be obtained by reference to certain specific examples which are provided herein for purposes of illustration only and are not intended to be limiting unless otherwise specified.

EXAMPLES

<Preparation of Glyceride Mixtures>

Glyceride Mixture A

Rapeseed oil fatty acid (650 parts) and glycerin (107 parts) were subjected to esterification in the presence of Lipozyme IM (product of Novo Nordisk Bioindustry Ltd.) at 0.07 hPa and 40° C. for five hours. The enzyme was separated from the reaction mixture through filtration, and the filtrate was subjected to molecular distillation at 235° C. The distilled matter was washed with water and deodorized at 235° C. for one hour, to thereby yield glyceride mixture A.

Glyceride Mixture B

Linseed oil fatty acid (650 parts) and glycerin (107 parts) were subjected to esterification in the presence of Lipozyme IM at 0.07 hPa and 40° C. for six hours. The enzyme was separated from the reaction mixture through filtration, and the filtrate was subjected to molecular distillation at 215° C. The distilled matter was washed with water and deodorized at 215° C. for two hours, to thereby yield glyceride mixture B.

Glyceride Mixture C

A mixture containing perilla oil (product of Ota Yushi) (300 parts), glycerin (120 parts), and calcium hydroxide (0.04 parts) was allowed to react at 220° C. for one hour under nitrogen. The reaction mixture was neutralized by use of phosphoric acid. The resultant mixture was degassed at 200° C. and 1.3 hPa by means of a thin film distillator. An initial boiling fraction (180° C., 0.4 hPa) was removed, to thereby remove glycerin. Subsequently, a non-boiling fraction (200° C., 0.07 hPa) was collected. Then, a non-boiling fraction (175° C., 0.1 hPa) was collected to remove glycerin again, thereby yielding glyceride mixture C.

Glyceride Mixture D

A mixture containing fish oil (product of Kao Corporation of Japan) (200 parts), glycerin (8 parts), and sodium methoxide (0.6 parts) was allowed to react at 100° C. for four hours under reduced pressure. The resultant reaction mixture was subjected to silica gel column chromatography (Wakogel C-200, product of Wako Pure Chemical) by use of hexane-ethyl acetate serving as an eluent for fractionation (first 100:0, then 90:10, then 80:20, and finally 70:30, VN). Then the solvent was removed from each fraction by evaporation. Target fractions were collected and combined, to thereby yield glyceride mixture D.

<Analysis of Prepared Glyceride Mixtures>

1. Glyceride Composition

Each of the thus-prepared glyceride mixtures was trimethylsilylated by use of a silylating agent (Silylating Agent TH, product of Kanto Chemical Co., Inc.), and analyzed by means of a gas chromatograph equipped with a capillary column (DBTM-1, product of J & W) and a hydrogen flame ionization detector. The results are shown in Table 1.

TABLE 1

| Glyceride mixture | (%) | | | |
|---|---|---|---|---|
| | A | B | C | D |
| Triglyceride | 13.5 | 14.1 | — | 56.1 |
| Diglyceride | 85.1 | 84.8 | 4.1 | 42.9 |
| Monoglyceride | 1.1 | 1.0 | 95.9 | 1.0 |
| Free fatty acid | 0.3 | 0.1 | — | — |

2. Composition of Fatty Acids from Which Glyceride Mixtures Have Been Produced Each of the prepared glyceride mixtures was fractionated by the method described in glyceride mixture D. A diglyceride fraction was obtained from each of the glyceride mixtures A, B, and D, whereas a monoglyceride fraction was obtained from glyceride mixture C. Each fraction was subjected to hydrolysis and methylation, and fatty acids contained in the fraction were analyzed through gas chromatography (Japan Oil Chemists' Society: Standard Methods for the Analysis of Fats, Oil, and Related Materials 2.4.1.2-1996 "method of preparing fatty acid methyl esters," and 2.4.2.2-1996 "fatty acid composition"). The results are shown in Table 2.

TABLE 2

| | A | B | C | D |
|---|---|---|---|---|
| C16:0 | 3.7 | 5.3 | 5.6 | 16.9 |
| C18:0 | 1.8 | 3.3 | 1.5 | 3.5 |
| C16:1 | — | — | — | 9.1 |
| C18:1 | 57.0 | 18.7 | 12.8 | 4.3 |
| C20:1 | 1.7 | — | — | 5.5 |
| C22:1 | 1.0 | — | — | 5.2 |
| C18:2 cis ω6 | 21.9 | 15.4 | 16.2 | 2.0 |
| C18:2 trans ω6 | — | — | 0.2 | — |
| C18:3 cis ω3 | 10.2 | 52.8 | 50.3 | — |
| C18:3 trans ω3 | 0.3 | 2.4 | 8.6 | — |
| C18:3 cis ω6 | — | — | — | 1.3 |
| C18:3 trans ω6 | — | — | — | — |
| C20:5 ω3 | — | — | — | 15.2 |
| C22:6 ω3 | — | — | — | 8.4 |
| cis ω3/(cis ω6 + trans + saturated) | 0.4 | 2.0 | 1.6 | NT |

— Not detected
NT Not tested

Example 1

Oil/fat compositions listed in Table 3 were produced.

TABLE 3

| Oil/fat composition | | Invention | | | | Comparison | | | |
|---|---|---|---|---|---|---|---|---|---|
| | | 1 | 2 | 3 | 4 | 5 | 6 | 7 | 8 |
| Glyceride Mixture (%) | Glyceride mixture A | | | | | 100 | | | |
| | Glyceride mixture B | 100 | 100 | | | | 100 | 100 | |
| | Glyceride mixture C | | | 100 | | | | | 100 |
| | Glyceride mixture D | | | | 40 | | | | |
| | Refined rapeseed oil | | | | 60 | | | | |
| Anti-oxidant (concentration: ppm) | Vitamin E | 1996 | 195 | 1996 | 196 | 200 | 200 | 200 | 200 |
| | Vitamin C palmitate | 100 | 98 | 100 | | 100 | | | |
| | Catechin (1) | | 24383 | | | | | 125 | |
| | Catechin (2) | | | | 47610 | | | | |
| Index of stability against oxidation | | 8.4 | 28 | 7.2 | 10.7 | 18.3 | 2.9 | 5.8 | 2.9 |

(Note 1)
Vitamin E: Mix Vitamin E (MDE-6000, product of Yashiro Co., Ltd.)
Vitamin C palmitate: product of Rosch
Catechin (1): Theaflan 90S (catechin content 70%, product of Ito En Ltd.)
Catechin (2): Sankatol No. 1 (catechin content 10%, product of Taiyo Kagaku Co., Ltd.)
(Note 2)
Anti-oxidant (concentration: ppm): Concentration in the oil/fat composition

Example 2

Diabetic obesity male mice C57BL/6J (7-weeks old, purchased from Nihon Kurea) were employed as a model of a life-style related disease. The mice were divided into groups, each group containing five mice and the average body weights of the groups being adjusted so as to be approximately equal to one another. The mice were bred for five months with a diet containing each of the oil/fat compositions produced in Example 1. The mice were dissected on the final day of breeding, and the body weight and fat weight around the epididymis were measured so as to evaluate the anti-obesity effect of the composition of the present invention.

Table 4 shows compositions of diets.

TABLE 4

(%)

| Diets | Invention | | | | Comparison | | | | | |
|---|---|---|---|---|---|---|---|---|---|---|
| | 1 | 2 | 3 | 4 | 5 | 6 | 7 | 8 | 9 | 10 |
| Oil/fat composition 1 | 10 | | | | | | | | | |
| Oil/fat composition 2 | | 10 | | | | | | | | |
| Oil/fat composition 3 | | | 10 | | | | | | | |
| Oil/fat composition 4 | | | | 10 | | | | | | |
| Oil/fat composition 5 | | | | | | | | 10 | | |
| Oil/fat composition 6 | | | | | | | | | 10 | |
| Oil/fat composition 7 | | | | | | | | | | 10 |
| Casein | 20 | 20 | 20 | 20 | 20 | 20 | 20 | 20 | 20 | 20 |
| Vegetable oil (rapeseed oil) | 15 | 15 | 15 | 15 | 5 | 25 | 25 | 15 | 15 | 15 |
| Sucrose | 13 | 13 | 13 | 13 | | 13 | 13 | 13 | 13 | 13 |
| Lard | 5 | 5 | 5 | 5 | | 5 | 5 | 5 | 5 | 5 |
| Catechin (1)* | | | | | | | 0.1 | | | |
| Mineral mixture | 3.5 | 3.5 | 3.5 | 3.5 | 3.5 | 3.5 | 3.5 | 3.5 | 3.5 | 3.5 |
| Vitamin mixture | 1 | 1 | 1 | 1 | 1 | 1 | 1 | 1 | 1 | 1 |
| Cellulose | 4 | 4 | 4 | 4 | 4 | 4 | 4 | 4 | 4 | 4 |
| Choline chloride | 0.15 | 0.15 | 0.15 | 0.15 | 0.15 | 0.15 | 0.15 | 0.15 | 0.15 | 0.15 |
| Starch | 28.35 | 28.35 | 28.35 | 28.35 | 66.35 | 28.35 | 28.25 | 28.35 | 28.35 | 28.35 |
| Body weight (g) | 31.8 | 29.9 | 31.4 | 31.5 | 28.1 | 36.1 | 36.5 | 34.2 | 33.8 | 33.1 |
| Epididymis fat weight (g) | 1.11 | 0.64 | 0.79 | 0.88 | 0.49 | 1.70 | 1.68 | 1.44 | 1.31 | 1.38 |

*the same as Example 1

As is clear from the results shown in Table 4, a remarkable reduction has been confirmed in body weight and fat weight around the epididymis of mice bred with any of the diets containing the oil/fat composition of the present invention.

Example 3

Flavored Oil

To oil/fat composition 2 (100 g) produced in Example 1, polyglycerin fatty acid ester (HLB=1; THL-3, product of Sakamoto Yakuhin K. K.) (0.1 g) and herb flavor (503056TH, product of Nihon Firmenich K. K.) (0.25 g) were added, and the mixture was uniformly mixed, to thereby produce a flavored oil.

Example 4

Brioche

| Composition: | |
|---|---|
| Flour (strong) | 100 parts by weight |
| Yeast | 5 |
| Yeast food | 0.1 |
| Sugar | 15 |
| Salt | 2 |
| Powdered skim milk | 4 |
| Whole egg | 50 |
| Water | 15 |
| Oil/fat composition 1 produced in Example 1 | 30 |

Raw materials other than oil/fat composition 1 were weighed and mixed by means of a mixer at low speed for 30 seconds. Subsequently, oil/fat composition 1 was added to the raw material mixture, and the resultant mixture was mixed at low speed for five minutes and at medium speed for 22 minutes. The obtained dough was leavened at 27° C. for 30 minutes, followed by low-temperature leavening at 5° C. for 15 minutes. The resultant dough was divided into 37-g portions, which were shaped into a round form. The shaped portions were leavened at 33° C. for 60 minutes and baked at 190° C. in an oven for nine minutes, to thereby produce brioches.

Example 5

Soft Capsules

Phytosterol (product of Tama Biochemical Co., Ltd.) (0.3 parts by weight) was added to oil/fat composition 4 (100 parts by weight) produced in Example 1, and the mixture was contained in oval-form soft-capsule bodies at 0.3 g/capsule, to thereby produce soft capsules.

Example 6

Tablets

Corn starch (44 parts by weight), crystaline cellulose (40 parts by weight), carboxymethyl cellulose calcium (5 parts by weight), silicic acid anhydride (0.5 parts by weight), magnesium stearate (0.5 parts by weight), and oil/fat composition 3 (10 parts by weight) produced in Example 1 were mixed, and the mixture was pelletized by a pelletizer, to thereby produce pellets (200 mg/pellet).

Example 7

Syrup

Refined white sugar (50 parts by weight), purified water (44.24 parts by weight), oil/fat composition 2 (5 parts by weight), hydroxycelulose (0.5 parts by weight), sucrose fatty acid ester (0.2 parts by weight), and sodium benzoate (0.06 parts by weight) were uniformly mixed, to thereby produce a syrup.

As described hereinabove, through ingestion thereof in a small amount without drastically changing the person's lifestyle, the highly harmless oil/fat composition of the present invention provides effects for reducing and preventing accumulation of body fat, for reducing and preventing accumulation of visceral fat, and for prevention and treatment of obesity; and exerts an excellent prevention and treatment effect on life-style related diseases through long-term ingestion. Thus, the composition of the present invention is useful for foods, pharmaceuticals, and pet food or feed.

Obviously, numerous modifications and variations of the present invention are possible in light of the above teachings. It is therefore to be understood that within the scope of the appended claims, the invention may be practiced otherwise than as specifically described herein.

This application is based on Japanese application JP 2001-129437 filed with the Japanese patent office on Apr. 26, 2001, the entire contents of which are hereby incorporated by reference.

What is claimed is:

1. An oil or fat composition comprising 5–100 wt. % of a monoglyceride and/or a diglyceride and at least one anti-oxidant selected from the group consisting of vitamin A, vitamin C, vitamin E, polyphenols and a mixture thereof and which exhibits an index of stability against oxidation (induction time as measured through a Rancimat test conducted at 100° C.) of 7 or higher, wherein said monoglyceride and/or the diglyceride contains, as fatty acid constituents, ω3 unsaturated fatty acids in amounts of 15–90 wt. %.

2. The oil or fat composition according to claim 1, wherein said fatty acid constituents are comprised of cis-ω3 unsaturated fatty acids, cis-ω6 unsaturated fatty acids, saturated fatty acids and trans-unsaturated fatty acids in a weight ratio of cis-ω3 unsaturated fatty acids/(cis-ω6 unsaturated fatty acids+saturated fatty acids+trans-unsaturated fatty acids) of 1–6, based on the fatty acid constituents of said monoglyceride and/or diglyceride.

3. The oil or fat composition according to claim 1, which further comprises a phytosterol in an amount of 0.05 wt. % or more.

4. The oil or fat composition according to claim 1, wherein said composition comprises a diglyceride as a mixture containing a 1,3-diglyceride and a 1,2-diglyceride in a proportion by weight of approximately 7:3.

5. The oil or fat composition according to claim 1, wherein said composition comprises a monoglyceride as a mixture containing a 1-monoglyceride and a 2-monoglyceride in a proportion by weight of approximately 9:1.

6. The oil or fat composition according to claim 1, wherein said percentage of the ω3 unsaturated fatty acids is 20–80%.

7. The oil or fat composition according to claim 1, wherein said percentage of the ω3 unsaturated fatty acids is 30–70%.

8. The oil or fat composition according to claim 1, wherein said composition exhibits percentage of the ω3 unsaturated fatty acids is 40–65%.

9. The oil or fat composition according to claim 1, wherein said fatty acids are selected from the group consisting of α-linolenic acid, stearidonic acid, eicosapentaenoic acid, docosapentaenoic acid, docosahexaenoic acid and a mixture thereof.

10. The oil or fat composition according to claim 1, wherein said monoglyceride and/or said diglyceride comprises as fatty acid constituents, C16–C22 unsaturated fatty acids in amounts of 55–100%.

11. The oil or fat composition according to claim 1, further comprising at least one anti-oxidant selected from the group consisting of phospholipids, butylhydroxytoluene, butylhydroxyanisole, tert-butylhydroquinone, propyl gallate, rosemary extracts, and a mixture thereof.

12. The oil or fat composition according to claim 1, wherein said composition exhibits an index of stability against oxidation of 9–50.

13. The oil or fat composition according to claim 1, wherein said composition exhibits an index of stability against oxidation of 11–40.

14. The oil or fat composition according to claim 1, wherein said composition exhibits an index of stability against oxidation of 15–30.

15. The oil or fat composition according to claim 1, wherein said composition exhibits an index of stability against oxidation of 20–30.

16. A food comprising the oil or fat composition of any one of claim 1, 2 or 3.

17. An agent for reducing or preventing accumulation of body fat, for reducing or preventing accumulation of visceral fat, or for preventing or treating obesity, which composition comprises the oil or fat composition of any one of claim 1, 2 or 3.

18. A method for reducing or preventing accumulation of body fat, which comprises ingesting the oil or fat composition of any one of claim 1, 2 or 3.

19. A method for reducing or preventing accumulation of visceral fat, which comprises ingesting the oil or fat composition of any of claim 1, 2 or 3.

20. A method for preventing or treating obesity, which comprises ingesting the oil or fat composition of any one of claim 1, 2 or 3.

21. A feed or pet food comprising the oil or fat composition of any one of claim 1, 2 or 3.

* * * * *